(12) United States Patent
Kudryavtsev et al.

(10) Patent No.: US 7,309,992 B2
(45) Date of Patent: Dec. 18, 2007

(54) GAS ANALYSIS METHOD AND IONISATION DETECTOR FOR CARRYING OUT SAID METHOD

(76) Inventors: Anatoly Anatolievich Kudryavtsev, ul. Kropotkina, d. 15, kv. 47, 197101 St.-Petersburg (RU); Alexander Borisovich Tsyganov, ul. Nalichnaya, d. 45, korpus 1, kv. 5, 199397 St.-Petersburg (RU)

( * ) Notice: Subject to any disclaimer, the term of this patent is extended or adjusted under 35 U.S.C. 154(b) by 228 days.

(21) Appl. No.: 10/531,536

(22) PCT Filed: Oct. 15, 2003

(86) PCT No.: PCT/RU03/00454

§ 371 (c)(1),
(2), (4) Date: Apr. 15, 2005

(87) PCT Pub. No.: WO2004/036206

PCT Pub. Date: Apr. 29, 2004

(65) Prior Publication Data

US 2006/0043279 A1    Mar. 2, 2006

(30) Foreign Application Priority Data

Oct. 18, 2002    (RU)    ............... 2002128663

(51) Int. Cl.
*G01N 27/62*    (2006.01)
(52) U.S. Cl. .............. 324/464; 324/459; 250/282
(58) Field of Classification Search ............... 324/464, 324/459; 250/282
See application file for complete search history.

(56) References Cited

U.S. PATENT DOCUMENTS

| | | | |
|---|---|---|---|
| 5,153,519 A | 10/1992 | Wentworth et al. | |
| 5,320,577 A * | 6/1994 | Tooru et al. | ............... 454/75 |
| 5,532,599 A | 7/1996 | Stearns et al. | |
| 5,767,683 A | 6/1998 | Stearns et al. | |
| 5,859,362 A | 1/1999 | Neudorfl et al. | |
| 6,037,179 A | 3/2000 | Abdel-Rahman | |
| 6,107,805 A | 8/2000 | Abdel-Rahman | |
| 6,163,031 A | 12/2000 | Abdel-Rahman | |
| 6,225,633 B1 * | 5/2001 | Sun et al. | ............... 250/389 |

FOREIGN PATENT DOCUMENTS

| | | |
|---|---|---|
| RU | 2 109 278 | 4/1998 |
| RU | 2 120 626 | 10/1998 |
| RU | 2 217 739 | 10/2002 |

* cited by examiner

*Primary Examiner*—Vincent Q. Nguyen
(74) *Attorney, Agent, or Firm*—J. Herbert O'Toole; Nexsen Pruet, LLC

(57) ABSTRACT

Chemical analysis of impurities in buffer gas is provided at various pressures up to atmospheric. Identification of the impurities is carried out by analyzing energy of electrons releases via ionization of the impurity atoms or molecules in their collisions either with excited atoms of buffer gas or with monochromatic photons. To produce excited metastable atoms a pulsed plasma is ignited between plane anode and cathode, and electrons energy is measured in afterglow by determining second derivative of electric current in dependence of voltage applied between these electrodes. Another way, electrons energy can be analyzed by positioning a grid between anode and cathode and by using an external radiation source to ionize the impurities in equipotential space between the grid and the anode. Inter-electrode gap and gas pressure must be chosen so that distortions in the electrons energy distribution due to collisions with buffer gas should not exceed a prescribed value.

41 Claims, 9 Drawing Sheets

GAS ANALYSIS METHOD AND IONISATION DETECTOR FOR CARRYING OUT SAID METHOD

FIELD OF THE INVENTION

This suggested invention relates to means for determination of gas mixtures composition and provides qualitative and quantitative analysis of chemical structure of impurities in a main (buffer) gas.

BACKGROUND OF THE INVENTION

There are known various gas detectors, in which the chemical composition is identified by mass analysis of ions occurring at the gas ionization (see, e.g. [1]). Measurement of the current of ions separated with respect to their charge-to-mass ratio provides determination of the qualitative and quantitative composition of the gas mixture. A common feature of these prior art methods with the one we are suggesting, is the ionization of impurities at an ionization chamber. One of disadvantages of these prior art approaches are large detector dimensions, because the ions with the different charge-to-mass ratio are selected and detected separately in a mass-spectrometer after a flight along a trajectory of definite length. Another disadvantage is the necessity to maintain a fairly high vacuum along this trajectory to prevent the ions from scattering in collisions with residual gas molecules.

Another way of identifying the gas composition is to measure the kinetic energy of electrons released at the gas ionization, if the energy of exciting particles, e.g. photons, is definite (see e.g. [2]). The difference between the known energy of photons and the measured kinetic energy of electrons provides information on the ionization potentials of atoms or molecules, from which the gas composition is identified. The energy distribution of photoelectrons and the known photo-ionization cross sections allow determination of the partial concentrations of the gas species. The common features of these prior art methods and the present invention are the impurities ionization in an ionization chamber and the current measurement. A demerit of this prior art way is a large size of the detector, as the electron energy analysis is also accomplished during a flight along a trajectory having a definite length. Besides, it is necessary to maintain a rather high vacuum along the trajectory to prevent the electrons from collisions with a residual gas.

There are known ionization detectors capable of detecting gas impurities presence from the variation in the ionization current when the gas is excited (e.g. [3-6]). Such detectors have a small size and can operate at various pressures, up to atmospheric one. U.S. Pat. No. 5,532,599 [7] is most closely related to the present invention in the entire combination of features and is chosen as the nearest analog. Their common features are that the impurity atoms or molecules are ionized in collisions with particles of definite energy (metastable helium (He) atoms) in an ionization chamber, the current across the electrode located in the chamber is measured as a function of the applied voltage, and the impurities are detected from the electrode current data. However, the nearest analog in question provides only an ascertainment of the fact that an impurity has appeared in the main gas but it fails to make a direct qualitative analysis (to identify the impurity atoms or molecules) or quantitative (to measure the impurity concentrations) one.

DISCLOSURE OF THE INVENTION

The present invention is aimed to develop the method of chemical analysis of gases which provides qualitative and quantitative analysis of a large class of substances in a wide range of pressures, up to and above of the atmospheric one. The aim is also to construct the ionization detector to implement said method, which would have a small size, a simple design, and could operate at various pressures of the gases being analyzed, also without using vacuum pumping devices. The suggested gas analysis method and the ionization detector on its basis can be used as stand-alone analysis means as well as in combination with gas chromatographs, atomic analyzers of a sample in an inductively-coupled plasma (ICP) source, atomic analyzers of solid state samples, including alloys, as well as in gas analyzers for gas medium control in various technology processes.

To reach this aim, the nearest analog for gas impurities detection from prior art, in which impurity atoms or molecules are ionized in collisions with particles of definite energy in an ionization chamber; the current across at least one of two electrodes located in the chamber is measured as a function of the voltage applied between said two electrodes, have been modified, as follows. According to the present invention, the pressure of the main gas and the ionization chamber geometry are to be chosen in such a way that a distance from any point inside of the chamber to the nearest wall or to one of said electrodes is less than a mean length of electrons displacement before they lose a prescribed portion of their kinetic energy. Also, equipotential space inside of said ionization chamber, where ionizing collisions occur, is to be provided. Also, a number of electrons with characteristic energy values produced in ionization of said atoms or molecules is determined from the current dependence on the voltage applied. Also, the data on the electron parameters are used to identify and determine the impurity species in the gas. This technical approach allows making a qualitative and quantitative analysis of a wide class of gaseous mixtures, using some kinds of main gas in various concentrations. The implementation of this technique is simple and compact because one needs only electrodes, a source of ionizing particles of definite energy, and appropriate means for registration of the electric current as a function of the applied voltage.

In particular, according to this invention, a noble gas may be used as the main gas, because it does not react with impurity atoms or molecules and does not introduce errors in the results of qualitative and quantitative analyses. Besides, the excited states of noble gas atoms normally have a higher energy than that of electrons produced by the impurity ionization. Therefore, there are no inelastic collisions between the electrons and the main gas atoms, so electrons characteristic energy is not distorted. Also, metastable atoms of a noble gas possess a sufficient energy to ionize most chemical compounds, so the excited noble gas can simultaneously be used as a source of particles with a definite energy to ionize the impurities.

In particular, according to this invention, helium may be used as the main gas. Its metastable atoms possess a high enough energy to ionize any gas except neon, which allows a chemical analysis of a large class of materials.

In particular, according to this invention, the main gas may be under pressure varying from 10 to $10^5$ Pa and higher. So, vacuum pumping devices for gas rarefaction may not be necessary, which simplifies the method.

In particular, according to this invention, the voltage applied to said two electrodes (the inter-electrode gap) is varied from zero to the ionization threshold of the main gas, and the amount of electrons with the characteristic energies is found from the second derivative of the current dependence on the voltage applied. So, the qualitative and quantitative analysis can be made in a simple way.

In particular, according to this invention, the equipotential space for ionization region inside of said ionization chamber may be provided by using a pulsed power source to produce an afterglow plasma inside of said chamber; the impurity atoms or molecules are ionized in collisions with metastable atoms or molecules of the main gas, formed at the said power source pulse effect. Said induced current is measured with a time delay following the power source pulse. The concentration and temperature of charged particles in the afterglow plasma are provided in such a way that at the moment of the current measurement the Debye length should be much less than the characteristic dimensions of the ionization chamber. It is one of the possible variants to create said equipotential space, since the afterglow plasma is electrically neutral and the electric field inside of it is close to zero. This simplifies the gas analysis because said pulsed energy source simultaneously provides both the afterglow plasma inside of ionization chamber to equalize the electrical potential of the chamber space and generates metastable atoms or molecules of the main gas with definite energy, which ionize the impurity molecules or atoms.

In particular, according to this invention, the pulsed power source may be a pulsed glow discharge between two said electrodes. It is the simplest source of plasma and metastable atoms.

In particular, according to this invention, the pulsed power source may be a pulsed laser radiation creating plasma in the inter-electrode gap. This allows extending the range of materials to be analyzed and the concentrations of impurities to be identified.

In particular, according to this invention, impurity atoms or molecules may be ionized by irradiating the afterglow plasma by photons of prescribed energy generated by an external source. It provides observation of additional groups of electrons with their characteristic energies different from those of electrons formed by ionizing the impurities by metastable atoms of the main gas. This extends further the analytical capabilities of the technique described.

In particular, according to this invention, impurity atoms or molecules may be ionized by photon irradiation, the photons being resonant with the main atoms or molecules. This increases the efficiency of impurity ionization by photons due the longer path length of photons in the ionization chamber, thus increasing the method sensitivity.

In particular, according to this invention, said electrodes may be implemented of a plane shape, mounted parallel each other; in such a way they also perform the function of the ionization chamber walls. This electrodes geometry and arrangement is simple, although, according to this invention, there is possible a variety of other configurations.

In particular, according to this invention, said ionization chamber may contain N insulated cathodes and an individual voltage value is applied to each cathode relative to one or several anodes. The current is measured across every cathode; the data array of current values measured is used to find the number of electrons with the characteristic energies, produced by ionization of impurity atoms or molecules. This provides to accelerate the analysis N times.

In particular, according to this invention, a conducting grid can be placed between said electrodes, said grid is electrically connected to the anode to create an equipotential space between them; the impurity atoms or molecules are ionized by irradiating the space between the grid and the anode by neutral particles of a definite energy from an external source. This is another way of creating equipotential space at the chamber region where ionizing collisions occur. This embodiment of the method provides one to decrease the concentration of ionized impurities and not to use afterglow plasma (the plasma-free detection variant). Also, the energy distribution of electrons in the absence of plasma can be reduced, thus improving the qualitative analysis. Photons or metastable atoms can be used as said neutral particles.

In particular, according to this invention, the electrodes and the grid may be plane-parallel to one another, the electrodes also acting as the ionization chamber walls. This is one of the simplest geometry implementing suggested method and detector.

In particular, according to this invention, impurity atoms or molecules are ionized by irradiating them by photons resonant with the atoms of the main gas. This provides a higher efficiency of impurity ionization by photons owing to their longer path length in the ionization chamber and thus increases the sensitivity.

In particular, according to this invention, the charge passed through the cathode is controlled; when the charge exceeds a prescribed value, the ionization in the space between the grid and the anode is stopped and an electric field is applied until the charged particles leave the inter-electrode gap; then the ionization and the current measurement are resumed. This maintains the equipotential space at the chamber region, where ionizing collisions occur, at the necessary level to avoid errors in the measurements.

In particular, according to this invention, N insulated cathodes may be mounted in the ionization chamber and an individual voltage is applied to each cathode relative to one or several anodes and corresponding one or several grids, respectively. The current across each cathode is measured individually; from the data array of current values measured one finds the number of electrons with the characteristic energies, produced in the ionization of the said impurity atoms or molecules. This increases the analysis rate N times.

In particular, according to this invention, analysis can be carried out of a sample target being sputtered by additional power source. Sputtered content, as the impurities, mixed with the main gas are delivered into the ionization chamber for analysis. Said additional power source may be, for example, a gas glow discharge with a sufficient current density. Also it may be a laser radiation focused on the sample introduced into ionization chamber or on one of the electrodes of said chamber to determine its composition. This extends the class of materials that can be analyzed by the suggested technique and detector.

In particular, according to this invention, it can be used said sample as a cathode atomized by a preliminary plasma discharge ignited by said additional power source. This provides analyses of metallic or conducting samples, extending the class of substances that can be analyzed by the method and detector suggested.

In particular, according to this invention, the impurity molecules can be subjected to a preliminary dissociation into atoms in the additional plasma discharge to analyze atomic composition of the impurities. This gives the opportunity to make a qualitative and quantitative analysis of chemical elements in a sample.

The essential features of the detector according to the present invention are similar to those essential features of the suggested method described above from the view of technical design and they are expressed in terms of characteristic features for a device in the invention claims.

Moreover, according to the present invention, the radiation source in the ionization detector may be filled with argon (Ar) and comprise a cylindrical window transparent to resonant radiation, two electrodes at the butt-ends of said window and a power source to ignite a gas glow discharge; the anode, cathode and the grid for photoelectron detection may be made as plane-parallel rings arranged co-axially and around of said cylindrical window; the radiation traverses only the space between the anode and the grid. This arrangement of the power source and the detection electrodes provides the optimal utilization of the radiation for photo-ionization because there is a large solid angle, in which the radiation passes into the space between the anode and the grid.

DESCRIPTION OF PREFERRED EMBODIMENTS OF THE INVENTION

The technical designs to implement the suggested method of gas analysis and the ionization detector are based on a qualitative model of the physical processes to be described below. The concrete details of the physical model described don't affect a broad understanding of the basic features of the present invention.

When atoms or molecules of an impurity A collide with particles B*, having a definite energy $E_p$, they become ionized to produce free electrons $\bar{e}$, if the B* particles energy is high enough:

$$A + B^* \rightarrow A^+ + B + \bar{e} \quad (1)$$

Figure 1:
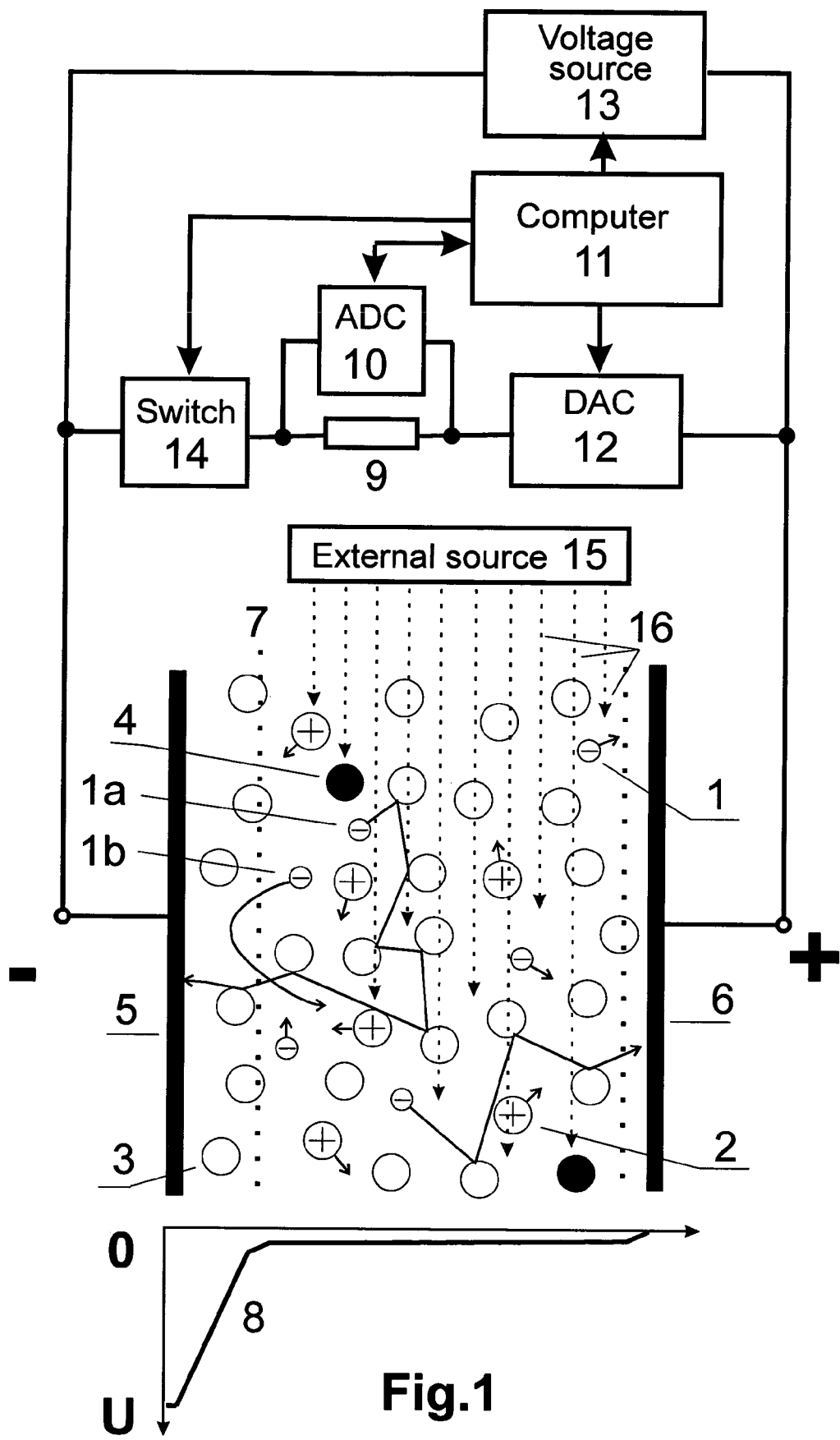
FIG. 1 is schematic block diagram of the ionization detector showing a schematic cross section of the ionization chamber with two plane-parallel electrodes, between which a pulsed gas glow discharge is ignited. The distribution of the electrical potential in the afterglow plasma in the inter-electrode gap is given also.

FIG. 1 shows schematically electrons 1 and impurity ions 2 produced by the collisions, as well as main gas atoms 3. As the particles of a definite energy $E_p$ there may be used, e.g., metastable or resonant excited atoms of the main gas 4 (the main gas also be referred as a buffer gas). Additionally, one can use photons with a given energy $E_p$ from an external source as said particles of a definite energy. The electrons released in this process gain kinetic energy $E_e$:

$$E_e = E_p - E_i \quad (2)$$

where $E_i$ is the ionization potential of an impurity atom or molecule under analysis.

Metastable atoms 4 can be produced by a pulsed plasma discharge ignited in the ionization chamber between cathode 5 and anode 6 when the buffer gas is a noble gas, say, helium. Electrodes 5 and 6 may serve as the chamber walls. Other walls can provide insulation between the cathode and the anode and may be partially or totally absent (not shown in FIG. 1 for this reason) if the analyzed gas mixture flow through the chamber is expedient. The external surfaces of the cathode 5 and the anode 6 (facing the conducting wires in FIG. 1) also have insulating coating, but it is not shown in FIG. 1 for simplicity.

A concentration ratio of the buffer gas and the impurities under analysis is to be in such a way that the most of the metastable atoms produced should be the buffer noble gas atoms. Following the discharge pulse end, a rapid irradiation of all excited atoms occur, and the afterglow plasma will mainly contain metastable atoms of the buffer gas with the definite energy $E_p$. Helium atoms have the energies 19.8 and 20.6 eV which are high enough to ionize all known impurity atoms and molecules, except for neon. The application of neon as a buffer gas may also be reasonable. In contrast to helium which has two metastable states with the energy difference of 0.8 eV and produces two groups of electrons with the energies defined by Eq. (2), the metastable levels for neon have an energy gap of about 0.1 eV. So, these levels of neon may be considered as one level to simplify the impurities identification. Other noble gases also have metastable states with a high energy $E_p$. Their usage as a buffer gas may also be reasonable because their metastable levels are convenient for ionization of some impurities. Also noble gases are chemically stable (they do not react with impurities), are common and remain gaseous in a wide temperature range. Moreover, noble gases consist exclusively of atoms with the lower excited states being quite high. Then the electrons produced in the ionization reaction (1) will undergo only elastic collisions with the noble gas in the ionization chamber, which are slightly distorting their characteristic energy $E_e$.

Moreover, impurities can be ionized by other metastable atoms or molecules with a sufficiently high energy $E_p$ according to Eq. (2), in dependence of conditions in which the ionization detector operates, on the buffer gas choice, and the impurities composition to be identified.

If we provide the equipotential space at the ionization chamber region where ionizing collisions occur, all electrons produced in these collisions will have a fixed kinetic energy relative to electrodes 5 and 6. If, following the present invention, the buffer gas pressure and the ionization chamber geometry are chosen such that the distance from any point in the chamber toward the electrodes 5, 6 or the nearest wall (not shown in FIG. 1) is smaller than the mean length of electrons displacement before they lose a prescribed portion of their kinetic energy, then the electrons 'wander' randomly in the equipotential space of the ionization chamber, being mainly subjected to elastic collisions with the buffer gas atoms until they find their way onto said electrodes 5, 6 or one of the walls to recombine there (to be lost). When an electron collides elastically with a buffer gas atom, it loses portion of its kinetic energy equal to $m/M_b$, where m is the electron mass and $M_b$ is the mass of the buffer gas atom. For example, $m/M_b$ ratio for helium is about 0.0001, so an electron loses only about 1% of its energy, undergoing 100 elastic collisions. The mean free path for an electron in elastic collisions equals:

$$L_e = 1/(N_b \cdot \sigma_e) \quad (3)$$

where $N_b$ is the concentration of the buffer atoms and $\sigma_e$ is the electron cross section for elastic collision with the buffer gas atom. The cross section value for a particular gas is known and is approximately equal to a gas kinetic one around $\sim 10^{-16}$ cm². Following each collision, the electron covers an average distance $L_e$ and then changes its direction randomly due to another collision, like a Brownian particle. According to the well-known diffusion equation, a Brownian particle suffers displacement to an average distance $L_e \cdot \sqrt{n}$ from the initial point after n collisions. Thus, an electron will lose, say, 1% of its energy when shifting in helium to an average distance ten times longer than the mean free path ($10 \cdot L_e$) away from the point where the ionization occurred. Let us introduce the electrons energy loss (distortion) level of $\delta_E$, equal to the ratio of the lost-to-initial energies. If in the case considered $\delta_E$ equals 1% for helium, then the ionization chamber geometry must be such that the minimum distance l from any point inside of the chamber to one of the walls or the electrodes should not be larger than $l_{min}$, equal to $10 \cdot L_e$ at the chosen helium concentration. Generally, $l_{min}$ is calculated using the values of $m/M_b$, $\sigma_e$, $N_b$ and the chosen level of $\delta_E$, whereas l obeys the condition $$l < l_{min} = \frac{\sqrt{\delta_E \cdot M_b / m}}{N_b \cdot \sigma_e} \quad (4)$$

Therefore, if the condition of Eq. (4) is fulfilled, the ionization chamber geometry may be rather arbitrary, because gas glow discharge plasma will occupy all the free space between the electrodes. However, it would be more reasonable to use a chamber as a parallelepiped with two opposite planes spaced at a distance $L = l_{min}$, being said electrodes 5 and 6 (FIG. 1). Due to it the 'dead volume' of the chamber, where the gas is not analyzed, is minimal. Eq. (4) does not impose restrictions on the transverse dimensions of electrodes 5 and 6, so they may be much larger than L. Therefore, the electrons will recombine on these electrodes 5,6 or the walls of the ionization chamber before they lose the energy portion larger than the given value of $\delta_E$. When the ionization chamber operates at the atmospheric pressure of the buffer gas (e.g., helium), the interelectrode gap must be about 0.1 mm. The transverse dimensions of the electrodes and, hence, their area are chosen in such a way that the total current across the electrode at an available density of electrons produced by the impurities ionization should be high enough to be reliably registered by conventional electronic circuits. It also follows from Eq. (4) and from the conditions for a gas glow discharge ignition that the range of working pressures may be from 10 to $10^5$ Pa and more.

The equipotentiality of that space inside of ionization chamber, where ionizing collisions occur, can be provided in various ways, for example, by creating afterglow plasma inside of ionization chamber in the gap between the electrodes 5 and 6, as is shown in FIG. 1. After the pulsed power source is switched off, the electron temperature $T_e$ in the afterglow plasma drops quickly to the buffer gas temperature of about 0.03-0.1 eV. For our purposes, the electron concentration $N_e$ is to be such that the Debye length $$L_D = \sqrt{T_e / (6\pi e^2 \cdot N_e)} \quad (5)$$

should be much more smaller than the geometrical size of the ionization chamber. It should be emphasized that the concentration of slow electrons $N_e$ in the afterglow plasma is much higher than that of the electrons produced by the impurities ionization in the afterglow. It is known that the electric field over the space occupied by the plasma is lower than a few $T_e$ values (see, e.g., [8]), so the electric field can be considered as practically zero and the space potential is uniform. Hence, the energy of electrons arising from the impurities ionization is defined by Eq. (2) and is independent of the coordinates of the point where they were born. If after the pulsed power source switch-off we apply voltage U to the gap between the electrodes 5 and 6, not exceeding the ionization potential for the buffer atoms, we can observe a current of predominantly positive ions flowing towards cathode 5 and an electron current flowing to anode 6. Thereat, the potential of the space inside of ionization chamber in FIG. 1 between the boundary plane 7 and anode 6 will be practically constant. At the same time, the electric field will be induced in a layer of $L_D$ thick between cathode 5 and plane 7, where the total applied voltage U drops, as is shown in curve 8 (the near-cathode potential drop). Simultaneously, a layer and a potential drop are observed near anode 6, but this drop is small (see, e.g., [8]). As a result, the equipotential space acquires a potential close to that of anode 6. This is due to the low velocity of ions, as compared with that of electrons, because the electron mass m is negligible as compared with the ion mass $M_b$.

The metastable atoms in the afterglow are also being lost (they are quenching to the ground state), and their lifetime can be found as $$1/\tau = 1/\tau_d + N_d \cdot v_m \cdot \sigma_{id} + N_e \cdot v_e \cdot \sigma_{ie} + N_m \cdot v_m \cdot \sigma_2 \quad (6)$$

where $N_d$ is the concentration of the impurity atoms or molecules; $\sigma_{id}$ is the cross section of inelastic collisions metastable atoms with impurities; $N_e$ is the electron concentration; $v_e$ is the average electron velocity in the plasma; $\sigma_{ie}$ is the cross section of inelastic collisions metastable atoms with electrons; $N_m$ is the concentration of metastable atoms; $\sigma_2$ is the cross section of inelastic pair collisions of metastable atoms; $v_m$ is the average velocity of metastable atoms; and $\tau_d$ is the diffusion lifetime of metastable atoms prior to their loss on the electrodes and chamber walls, defined by the relation $$\tau_d = L^2 \cdot N_b \cdot \sigma_b / v_m \quad (7)$$

where $\sigma_b$ is the cross section of elastic collisions between metastable atoms and the buffer gas.

During their random wandering in the equipotential space, electrons 1 find their way to cathode 5 with their initial kinetic energy almost totally preserved, because, according to Eq. (4), an electron is lost on the electrodes or on the walls ('going out of play') before it has lost any significant portion of its energy. When electron 1 flies into the uniform electric field of the near-cathode voltage drop (the region between planes 5 and 7 in FIG. 1), it moves at some random angle to the field vector and suffers retardation. It follows from equations of motion in a uniform electric field that at a given negative potential U of the cathode 5, an electron (e.g., 1*a* in FIG. 1) possessing a sufficient kinetic energy $E_e$ and a velocity vector located in some cone around the field vector reaches the cathode surface, making its contribution to the current. Otherwise, an electron (e.g., 1*b* in FIG. 1) is reflected by the retarding potential of cathode 5 to go back to the equipotential space. Then it may make another attempt to reach cathode 5 or, eventually, be lost on the anode 6 or on the chamber walls. If an electron, already being in the said electric field, is suffered an elastic collision with a buffer gas atom, it will not change its absolute energy; rather, it is only its velocity vector direction that may change randomly. Therefore, the random character of the angular distribution of the velocity vector relative to the field vector remains even after elastic collisions occurring in the layer between planes 5 and 7. The electron velocity distribution in the equipotential space of the ionization chamber can be described by the distribution function F(v), where v is the electron velocity module and F(v)dv corresponds to the number of electrons with a velocity in the range of v to v+dv. In particular, the distribution function $$F\left(\sqrt{2(E_p - E_i)/m}\right)$$

defines the concentration of electrons produced by the ionization of impurity atoms or molecules with the ionization potential $E_i$. The integration over all electron energies and over all angles, at which electrons enter the uniform electric field of the layer (we assume the angular distribution of electrons to be uniform due to their random wandering in the equipotential space), gives the current-voltage characteristic, i.e., the dependence of the electron current $I_e$ across the plane cathode on the applied voltage U and on the form of F(v) (see, e.g., [8]):

$$I_e = \frac{1}{4} e \cdot N_e \cdot S \cdot \int_{\sqrt{2eU/m}}^{\infty} v \cdot F(v) \cdot \left(1 - \frac{2e \cdot U}{m \cdot v^2}\right) \cdot dv \quad (8)$$

where e is the electron charge and S is the electrode area.

At the same time the positive ion current across the cathode 5 is defined by the product of the layer area (plane 7) around the cathode 5 and the density of the ion diffusion flux at the layer boundary. The surface of the cathode 5 must be smooth enough for the layer thickness to be small as compared with the local curvature radius of the cathode surface. In that case, the electric field in the layer will be uniform and the layer surface area will be practically independent of the applied voltage U. The positive ion current across cathode 5 remains nearly constant with varying U, so their contribution can be subtracted from the resultant current-voltage characteristics of the detector.

Depending on the applied voltage, the current between electrodes 5 and 6 is measured in a routine way, for example, from the voltage drop across resistor 9 connected to this circuit. The voltage from the resistor 9 must be low enough to avoid errors in the current-voltage characteristic of the detector, so it is amplified with conventional electronic circuits. Then the current-voltage characteristic is plotted. For example, the voltage from resistor 9 is applied to the input of an amplifier with an analogue-digital converter (ADC) 10 and further to computer 11 for the data acquisition and processing. A digital-analogue converter (DAC) 12 is also connected to the computer. The negative voltage at the DAC output is applied to cathode 5 in the range of 0 to 25 V (the ionization threshold for helium atoms). Computer 11 also controls pulsed power source 13 for a glow discharge ignition to create an afterglow plasma. It is designed in a conventional way, for example, using a high voltage transistor switch for a pulsed commutation of the DC negative voltage 200-600 V to the cathode 5. The repetition rate of the pulses from said power unit 13, their duration and amplitude can also be controlled by computer 11. For ADC 10 and DAC 12 there are used conventional electronic circuitries which are capable to gate the input and output signals, if necessary. As a pulsed power source for creating plasma there may be used a flux of fast charged particles (electrons or ions) generated by an accelerator, a pulsed laser, etc.

The measuring system operates as follows. Computer 11 triggers a discharge current pulse from power unit 13 and, with a time delay after the discharge pulse end and the plasma cooling in the gap between electrodes 5 and 6, turns on the switch 14 protecting the measuring circuitry comprising resistor 9, ADC 10 and DAC 12. The delay time of turning on the switch 14 should not be longer than the lifetime τ of metastable atoms in the particular discharge conditions.

As a protecting element 14 there can be used a high voltage diode connected by its anode to cathode 5; the diode is turned off at high negative voltage during the pulse generation by power unit 13 but it is turned on by the negative voltage from DAC 12 during the afterglow. When the transient processes are over after switch 14 is turned on, computer 11 measures the voltage on resistor 9 using ADC 10 and then can set a new voltage value at DAC 12. This operation is repeated after each discharge current pulse from power unit 13. Data from ADC 10 are summed up and averaged by computer 11 for each set value of the DAC 12 voltage, thus providing the current-voltage characteristic. One can also register the total current-voltage characteristic or its part after a single discharge pulse from power unit 13. For this, the necessary number of consecutive current values are recorded by ADC 10 in afterglow at various values of the cathode-anode voltage set by DAC 12 and computer 11. There should be a time delay between each DAC 12 voltage setting and the consecutive ADC 10 current recording to avoid the effect of transient processes on the measurement accuracy.

According to Eq. (2), the characteristic energy $E_e$ of electrons generated by the impurity ionization may vary with the impurity ionization potential from zero to the exciting particle energy. The upper limit of the acceptable exciting particle energy can be taken to be the ionization energy of a buffer atom, since higher energies will induce ionization of the buffer gas itself, and the contributions of the impurities would be hard to identify against this background. Therefore, by measuring the current-voltage characteristic in the applied voltage range from zero to the ionization potential of a buffer atom, one can find with Eq. (8) the velocity distribution function for electrons F(v) (and respective electrons energy distribution f($E_e$)), and the amount of electrons generated in the ionization of the impurity of interest. To illustrate, by differentiating Eq. (8) twice in U, we get $$F(\sqrt{2eU/m}) = \frac{4m}{e^2 \cdot S \cdot N_e} \cdot U \cdot \frac{d^2 I_e}{dU^2} \quad (9)$$

Hence, the measured current-voltage characteristic differentiated twice gives a curve containing peaks, each of which corresponds to the group of electrons produced by the ionization of a particular impurity. The energy $E_e$ of these electrons and, therefore, the positions of the respective peaks in the inter-electrodes voltage applied scale are defined by Eq. (2). The double differentiation can be performed in various ways, for example, by a straightforward numerical differentiation of the measured current-voltage characteristic with using various smoothing procedures for the data, if necessary. One can also employ various electronic circuits using modulation of the applied voltage U with a weak alternating signal ΔU of frequency ω and a registration of the current at the frequency ω to obtain the first derivative, or at the frequency 2ω to obtain the second derivative.

From the peak positions observed and the corresponding $E_i$ values, one can identify the impurities present in the buffer gas. The known rate constants $k_{id}$ of the impurity ionization by metastable buffer atoms and the current value $I_{ed}$ of electrons with the energy $E_p$–$E_i$ provide the partial impurities concentrations $N_d$ for the case of plane-parallel electrodes:

$$N_d = I_{ed}/(e \cdot A \cdot k_{id} \cdot N_m \cdot S \cdot L) \quad (10)$$

where A is a dimensionless factor depending on the ionization chamber geometry and equal to about 0.5, indicating that only about half of the electrons are able to reach the cathode, while the other half is lost on the anode and the chamber walls. The concentration of metastable atoms $N_m$ can be found by standard spectroscopic techniques, for example, from the data on the resonance radiation absorption or the photo-ionization from the metastable level. This can also be done by finding the current $I_{e2}$ of electrons produced in ionization of two colliding metastable atoms from the measured current-voltage characteristic and from the following expression:

$$N_m = \sqrt{I_{e2}/(A \cdot e \cdot k_{i2} \cdot S \cdot L)} \quad (11)$$

where $k_{i2}$ is the rate constant of collisional ionization of two metastable atoms. The absolute impurities concentrations can be also found if one adds to analyzed mixture a known impurity of a given concentration and compares the ionization currents using Eq. (10).

Additional ionization of the impurity atoms or molecules in the afterglow plasma can be provided by neutral particles from an external source 15. These may be photons with a definite energy sufficient to ionize the impurities but too low to ionize the buffer gas. A source 15 of such neutral particles 16 may be a laser or a gas glow discharge in a noble gas. Such a glow discharge is known to emit predominantly resonant photons corresponding to transitions from low excited states to the ground state of the noble gas atom; these photons have a high enough energy to ionize impurities. For instance, a helium glow discharge emits resonant photons with the energy of about 21 eV and sufficient monochromaticity.

An afterglow plasma is irradiated by photons 16 and the energy distribution function F(v) of photoelectrons produced by the impurities ionization is derived, as described above. In this way, the ionization chamber is shielded from undesirable penetration of charged particles generated by external source 15 by placing electrodes between them to trap that particles or by placing a window transparent to photons only. One can also place there a diaphragm to form the photon flux 16 towards a prescribed region of the ionization chamber. The noble gas in the source 15 may be of different kind from the buffer gas in the ionization chamber.

Additional ionization of impurity atoms or molecules can also be provided by using photons resonant to the buffer gas if source 15 and the ionization chamber are filled with the same noble gas. The ionization efficiency and the characteristic electron current are increased here due to the longer path length of the photons inside of the ionization chamber owing to the 'radiation trapping' effect and due to the additional impurities ionization in collisions with resonantly excited buffer gas atoms.

The combination of fields in the ionization chamber, suggested by the present invention, can also be achieved (see FIG. 2) by placing a conducting grid 17 between cathode 5 and anode 6 and by applying to the grid the same potential as to anode 6 to create an equipotential space between them. Insulators are positioned between grid 17 and cathode 5 and at external surface of cathode 5 and anode 6 (not shown in FIG. 2 for simplicity). A voltage is applied between anode 6 and cathode 5, with the potential distribution in the ionization chamber depicted by curve 18. To ionize the impurity atoms or molecules, neutral particles of definite energy are introduced in the space between grid 17 and anode 6; these may be metastable atoms or photons 16 from external source 15. Measures should be taken to minimize the impurity ionization in the space between grid 17 and cathode 5, because of the energy of generated here electron will be added to the potential at the point where it is born, so the energy distribution of such electrons will be smeared. To avoid this, neutral particles flux 16, for example, can be directed in such a way that it passes through the region between grid 17 and anode 6 without entering the region between the grid and cathode 5. The configuration of electrodes 5, 6 and grid 17 may be arbitrary, provided that the condition of Eq. (4) is fulfilled. But optimal is the variant when the electrodes and the grid have a planar-parallel configuration, spaced at a distance of about L=$l_{min}$, and electrodes 5 and 6 also act as the ionization chamber walls. In that case, the electric field between the grid 17 and cathode 5 is uniform, with the 'dead' volume being smallest. After the ionization, the electrons and ions move through the equipotential space between anode 6 and grid 17 and in a uniform electric field between grid 17 and cathode 5, similarly to the movement between planes 6 and 7 and planes 7 and 5 in the plasma discharge shown in FIG. 1. Therefore, Eq. (9) is valid here, too, and can be used for finding the amount of electrons with the characteristic energy, arising at ionization of impurity atoms or molecules, from the current-voltage curve. Using photon ionization, the concentrations of the identified impurities may be determined from their known photo-ionization cross sections $\sigma_{ip}$, the measured photon flux J and the photon path length D in the space between anode 6 and grid 17:

$$N_d = I_{ed}/(e \cdot A \cdot \sigma_{ip} \cdot J \cdot D) \qquad (12)$$

while the factor A should be additionally multiplied by the transparency coefficient of the grid 17. The detector can be similarly calibrated by adding a known impurity with a given concentration to the buffer gas.

In contrast to the plasma variant, where the current can be measured only in the afterglow and only when the Debye length of the plasma (5) is much smaller than the dimensions of the ionization chamber, this modification provides an opportunity for continuous current measurement during the ionization of impurity atoms or molecules irradiated by neutral particles 16.

Moreover, according to the present invention, it is possible to use photons resonant to the buffer gas atoms to ionize the impurity atoms or molecules in the ionization chamber. In that case, the ionization efficiency increases due to the longer path length of the photons in the ionization chamber and to the additional ionization of the impurities in collisions with resonantly excited buffer atoms.

Furthermore, intensive impurity ionization may lead to the accumulation of a considerable space charge of positive ions in the region between grid 17 and anode 6, because the ions have no time to recombine on the electrodes and chamber walls. This space charge violates the equipotentiality in this region, distorting (shifting or smearing) the energy distribution of the photoelectrons. To avoid this, computer 11 may control the current to cathode 5 starting at the moment the source 15 is turned on. If this current exceeds a certain threshold for some period of time, the ionization in the region between grid 17 and anode 6 is stopped by, say, turning off the source 15. Using electric switches, a negative potential is applied to anode 6 relative to grid 17, which is close to the potential of cathode 5, until the ions leave the inter-electrode gap. Then the ionization is resumed with controlled decreasing of the photon flux from source 15. The controlled current threshold is defined by the ion concentration in the region between grid 17 and anode 6, at which the space charge provides a definite level of distorting electric field in this region and it can be calculated or found experimentally from the chosen signal distortions level from the known impurity.

Figure 3:
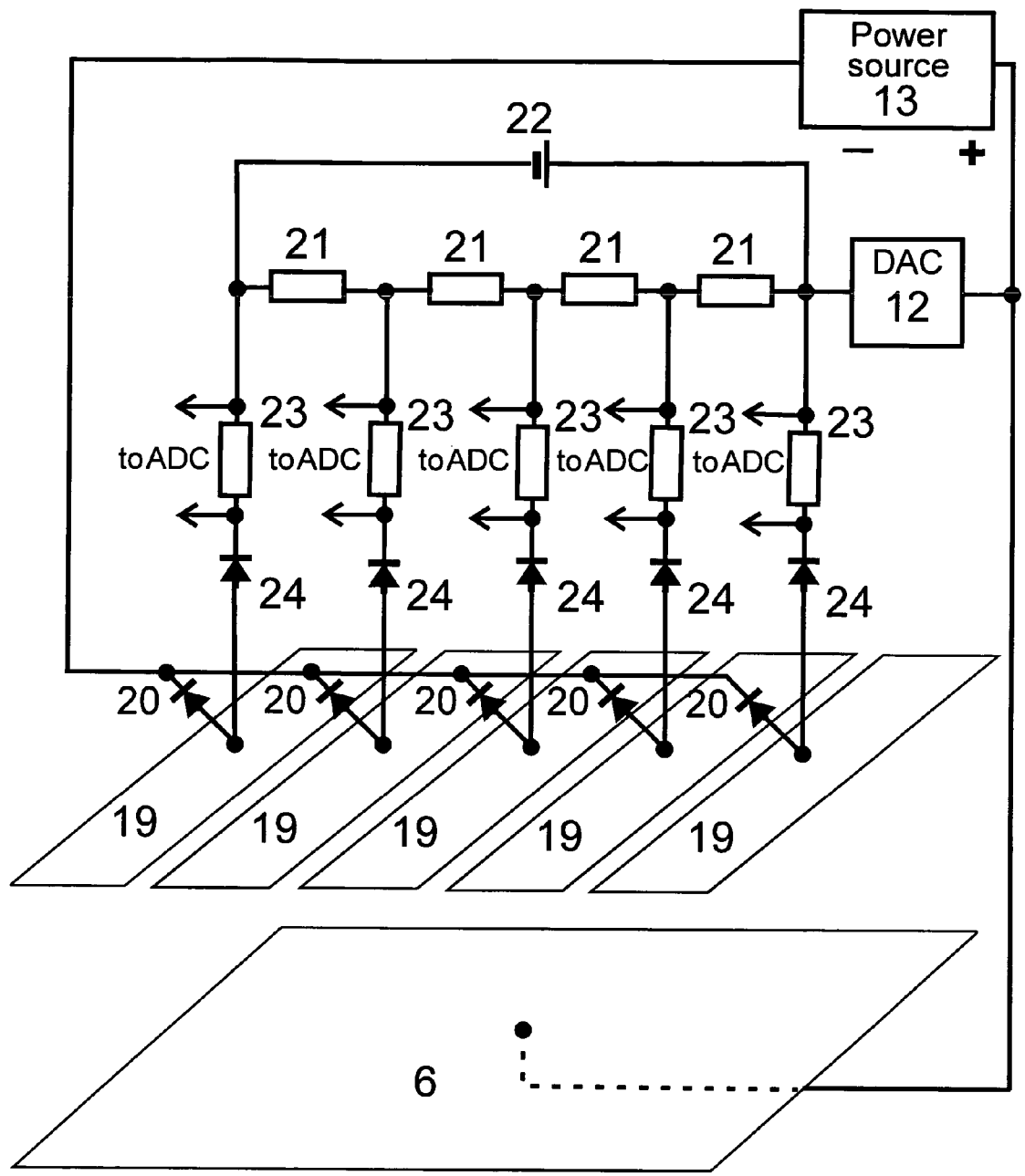
FIG. 3 is a block diagram of the ionization detector with a pulsed glow discharge between plane-parallel electrodes and a stereometric view of the ionization chamber. The cathode is subdivided into N insulated segments, with current-voltage characteristic being measured individually for each said segment.

FIG. 3 shows that cathode 5 in the ionization chamber with afterglow plasma can be made up of several (N) insulated segments 19. The voltage for glow discharge ignition by the pulsed power unit 13 is applied to each segment 19 through diodes 20 in order to measure the current of each segment individually during the afterglow. The voltage value is individual for each segment 19 and is the sum of the output voltage of DAC 12 and the output from a voltage divider consisting of resistors 21 connected to power supply 22. The nominal values of resistors 21 may be selected in such a way that the potential difference between neighboring segments 19 corresponds to the chosen current-voltage measurement step value, providing minimal distortions in the electric field at the segment boundaries. The current from cathode 5 is responsible for the voltage drops across resistors 23, these voltages are measured, e.g., by a set of ADCs or sample-and-hold circuitries connected to a multichannel analogue multiplexor and further to an ADC. This ADC consecutively measures the signals from those sample-and-hold circuitries. These connections to ADC (or sample-and-hold circuitries) are shown with arrows in FIG. 3. Diodes 24 are used to protect the measuring circuits from the pulsed voltage of power unit 13. A possible shift of the current-voltage characteristic due to the voltage drop across resistors 21 can be accounted for by Ohm's law due to the values of resistors 21 and 23 are known. In this way, one can get several points in the current-voltage characteristic simultaneously during one current pulse from the unit 13, rising analysis rate by N times. Having mounted a sufficient number of segments 19 and having applied the set of voltage values respective to chosen electron energy spectra intervals, we can identify the impurities even within a single discharge cycle.

Figure 4:
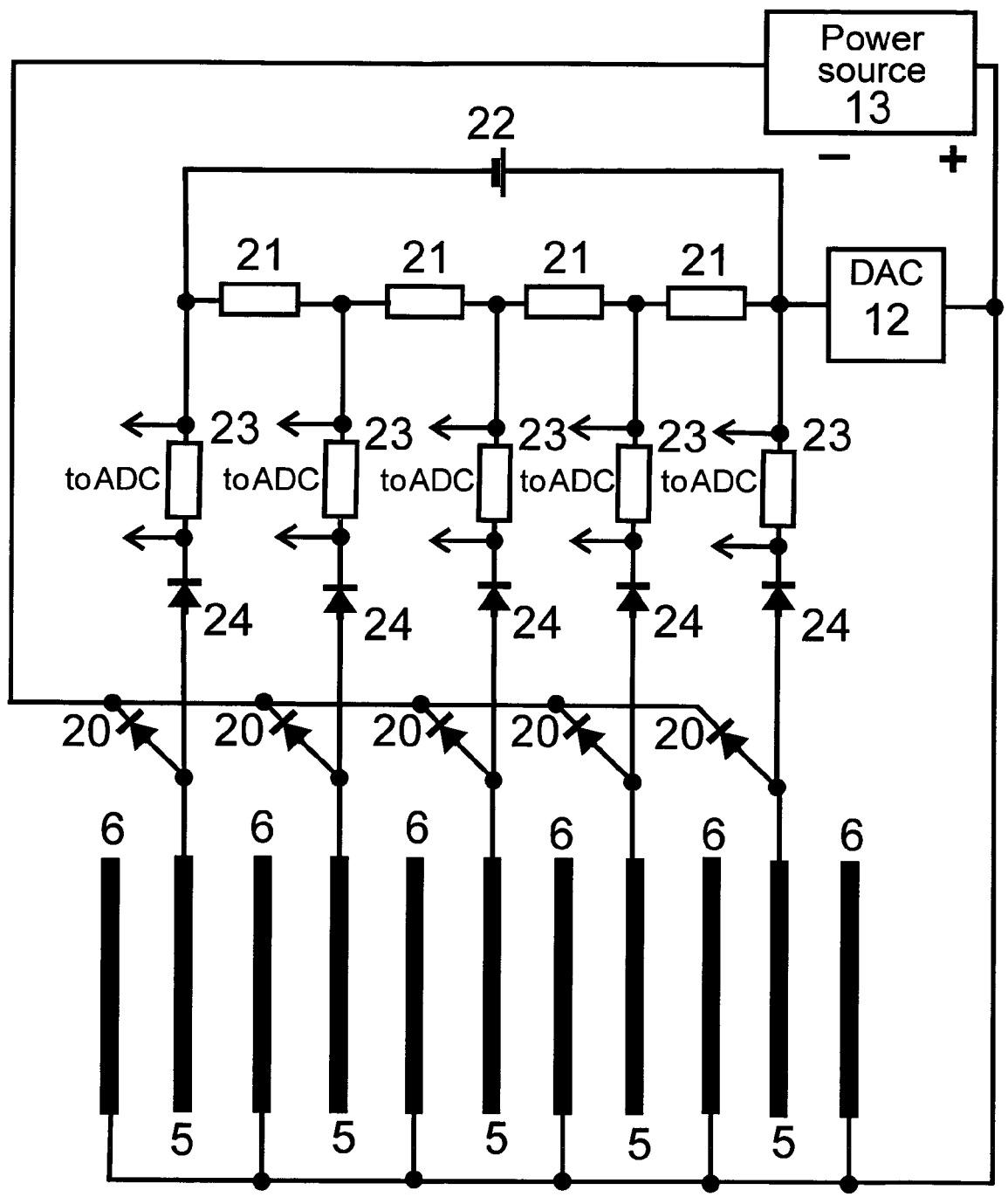
FIG. 4 is a block diagram of the ionization detector with a pulsed glow discharge in the gaps between the plane-parallel electrodes and a cross section of the ionization chamber with N cathode-anode pairs.

It is also possible to place N number of cathode 5-anode 6 pairs in the ionization chamber, as shown in FIG. 4. An individual voltage is applied to each cathode 5 to register the individual current values in the afterglow; with all anodes 6 connected to each another. Insulators are positioned between cathodes 5 and anodes 6, as well as from the outside surface of uttermost electrodes (not shown in FIG. 4 for simplicity). If it is necessary to decrease the detector size, each cathode 5 can be designed as two metallic sheets with a dielectric between them, so that the each sheet would serve as an individual cathode with an individual measuring circuit connected to it.

Figure 2:
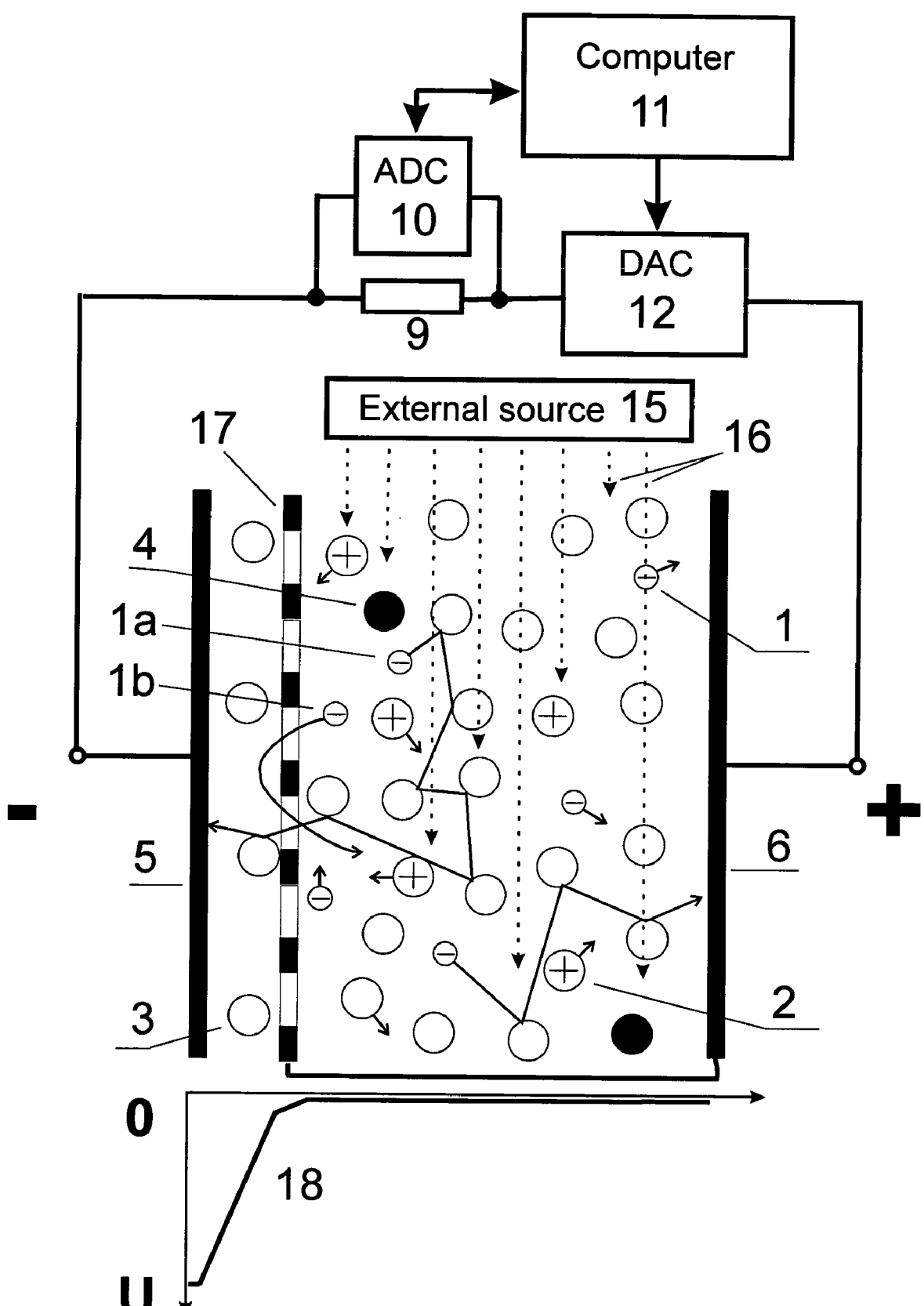
FIG. 2 is a block diagram of the ionization detector without afterglow plasma generation and a schematic cross section of the ionization chamber with two plane-parallel electrodes with a plane conducting grid between them. A flux of ionizing photons from an external source is directed into the chamber. The electric field distribution in the gap between electrodes is given.
Figure 5:
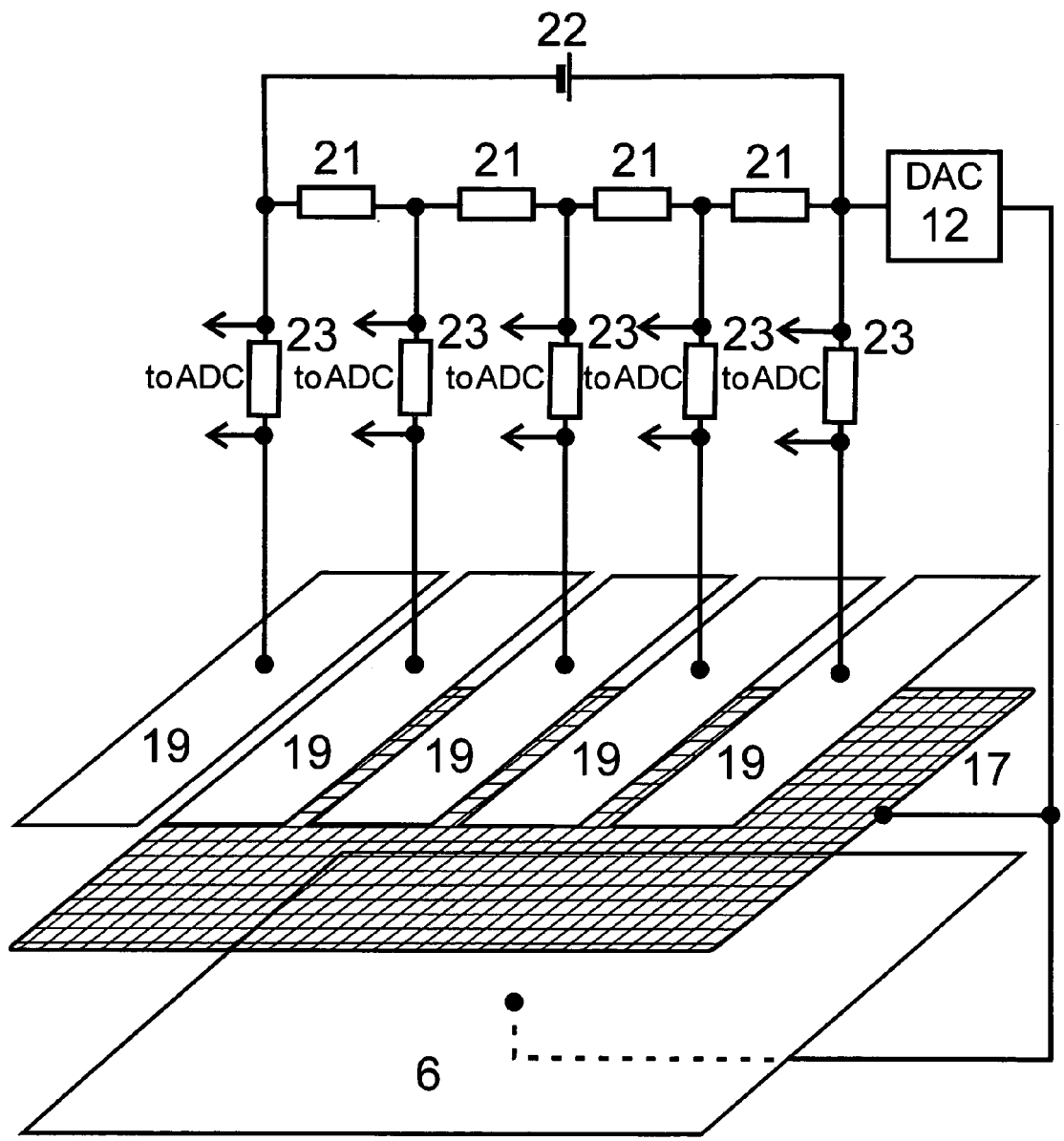
FIG. 5 is a block diagram of the ionization detector without afterglow plasma generation and a stereometric view of the ionization chamber with a grid between the cathode and the anode. The cathode is subdivided into N insulated segments, while the grid and the anode are common to all of the N segments.

FIG. 5 illustrates an ionization chamber with grid 17 placed between a cathode consisting of N segments 19 and anode 6 to analyze electrons produced in the gap between anode 6 and grid 17 when the particles from external source 15 (not shown in FIG. 5) affect the gas, a variant similar to the one in FIG. 2 with a single cathode 5-anode 6 pair. This also accelerates the impurity analysis by N times.

Figure 6:
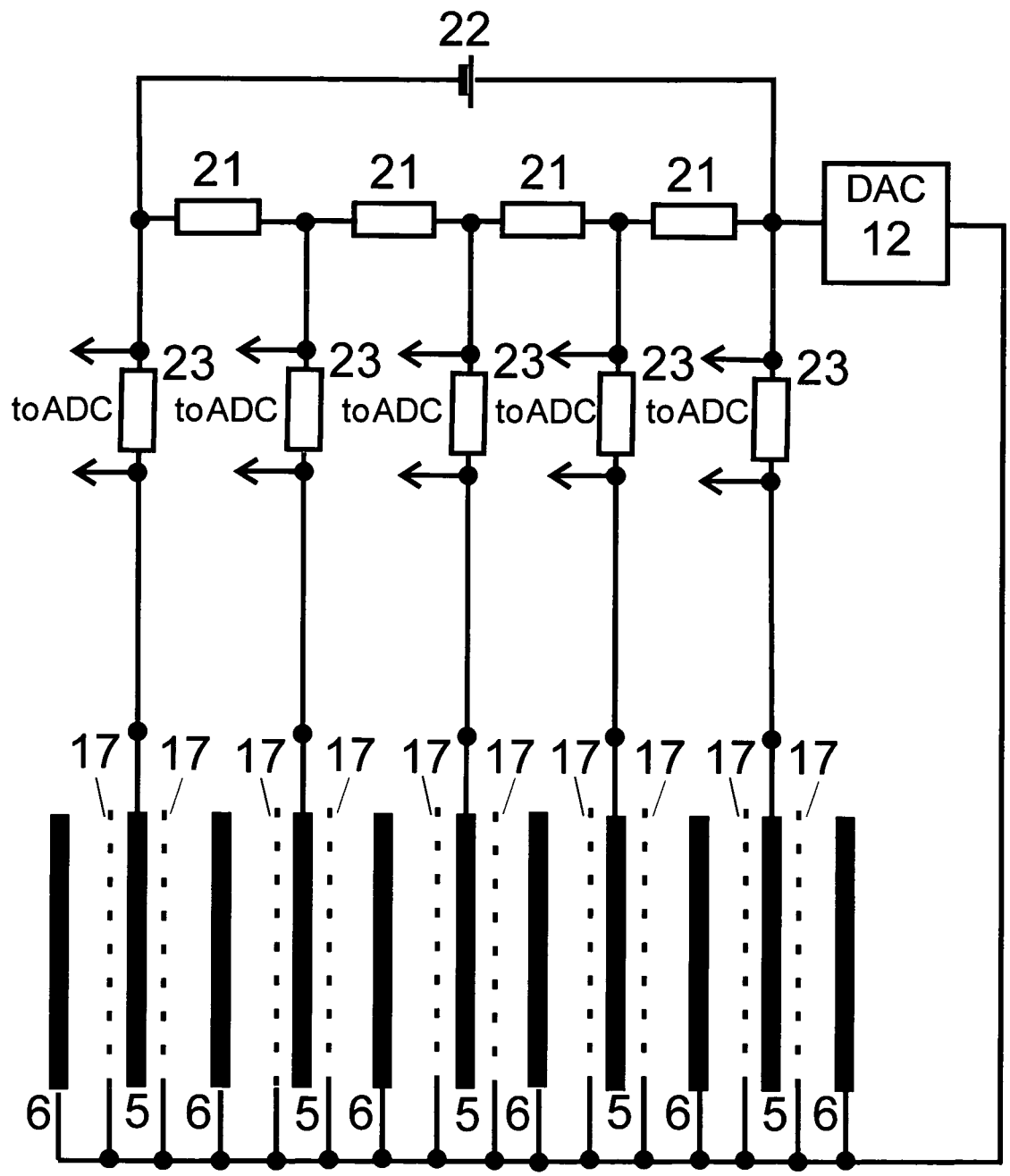
FIG. 6 is a block diagram of the ionization detector without generation of afterglow plasma and a cross section of the ionization chamber with N pairs of cathode-anode and with grids between them.

FIG. 6 shows an ionization chamber with grids 17 between N cathode 5-anode 6 pairs to analyze electrons generated in the gaps between each anode 6 and grid 17 by the particles from external source 15 (not shown in FIG. 6), similarly to the variant with one cathode-anode pair in FIG. 2. To reduce the detector size, cathodes 5 can be made as a dielectric plate with two metallic surfaces, as described for the variant illustrated in FIG. 4.

Figure 7:
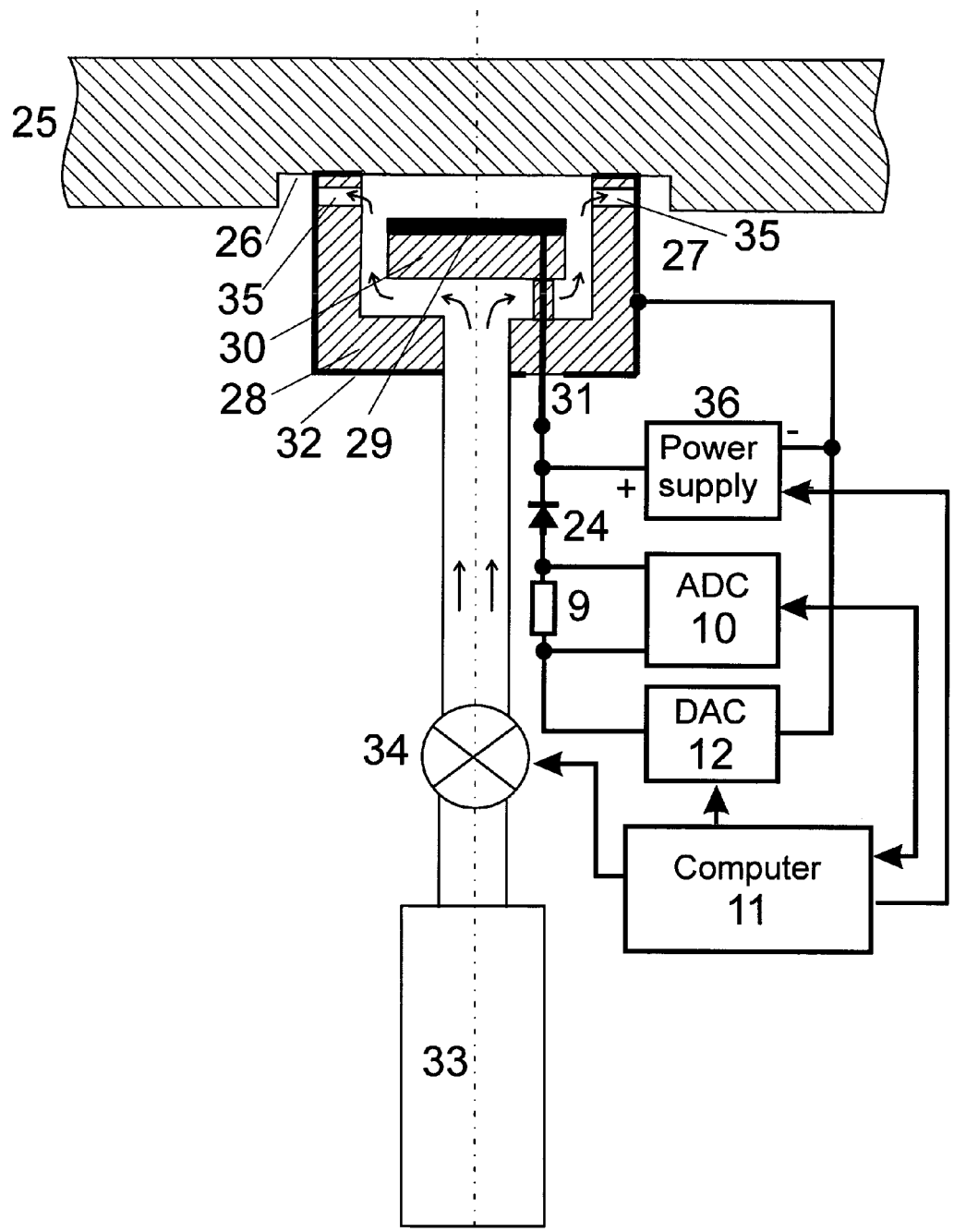
FIG. 7 is a cross section of the ionization detector and a block diagram of the setup for identification of elemental composition of a conducting sample atomized by a pre-ignited gas glow discharge.

Besides, FIG. 7 demonstrates a variant, where material of a sample target 25 can be analyzed as gas impurity, when the target is atomized using an additional power source. For this, a cylindrical depression 26 with a plane bottom is made (e.g., with a mill) in the sample 25 and an analyzer frame 27 accomplished from a dielectric 28 is installed on it. A cylindrical electrode 29 is mounted in the analyzer frame 27 with a flat butt side facing the plane surface 26. The opposite butt side of electrode 29 is covered with an insulator 30 and an insulated electric lead 31 is passing it through to outside of analyzer frame 27. The outer surface of analyzer frame 27, including the surface contacting plane 26, has a metal coating 32. A container 33 filled with a buffer gas is connected to analyzer frame 27 through a pressure regulator with a valve 34. The buffer gas, for example helium or neon, is supplied under some excess pressure into analyzer frame 27 to come out (shown with arrows) through openings 35 in the analyzer frame. Atmospheric gases are pushed out of the gap between the electrode 29 and plane surface 26 by the buffer gas having the appropriate flow rate. This buffer gas flow also prevents the atmospheric gases from getting back into this gap.

As an additional power source for atomizing the sample 25 it can be used a thermic heating of the sample surface, or it may be a laser radiation. As most simple, it may be also a pulsed glow discharge where the plane surface 26 of the sample to be analyzed is used as the cathode. The positive voltage pulse applied to electrode 29 from power unit 36 should be of such value that the discharge current density is high enough to create the necessary concentration of the sample atoms in the gap between the electrode 29 and the sample surface 26. At this moment, diode 24 is turned off to protect the measuring circuit made up of resistor 9, the amplifier with ADC 10 and the DAC 12 from the voltage pulse of unit 36. The time delay following the current pulse of unit 36 should not be larger than the lifetime of the sample atoms sputtered prior to their deposition on the analyzer walls and electrodes; then a positive voltage from the DAC 12 controlled by computer 11 is applied to electrode 29. Thus protective diode 24 is turned on, and the current across electrode 29 is measured using resistor 9 and the amplifier with ADC 10. Computer 11 also controls pulsed power unit 36 and the pressure regulator with a valve 34. After the buffer gas flow is turned on, some current pulses by unit 36 are generated to clean the sample surface 26 from adsorbed atmospheric gases and contaminants left by the sample depression 26 milling. Then the measurement of the current-voltage characteristic is started. If the mixture in the gap between electrode 29 and sample surface 26:

(1) contains charged particles of such concentration and temperature that the Debye length, according to Eq. (5), is sufficiently low and (2) if the concentration of metastable atoms of the buffer gas is sufficient for a reliable detection of electrons with the characteristic energy after the effect of the additional power source 36, one can identify the impurities in the way described above for a variant on FIG. 1. If one of the above conditions is violated, an additional pulsed glow discharge can be ignited in this mixture to provide the necessary conditions. Also, the mixture can be excited by photons or metastable atoms to carry out the analysis according to the variant with two electrodes and a grid (see above). In that case, the mixture to be analyzed must be supplied into the ionization chamber fast enough to provide a shorter time delay between the sample atomization and the impurity analysis than the lifetime of the sputtered impurity atoms in the buffer gas prior to their deposition on the walls.

Figure 8:
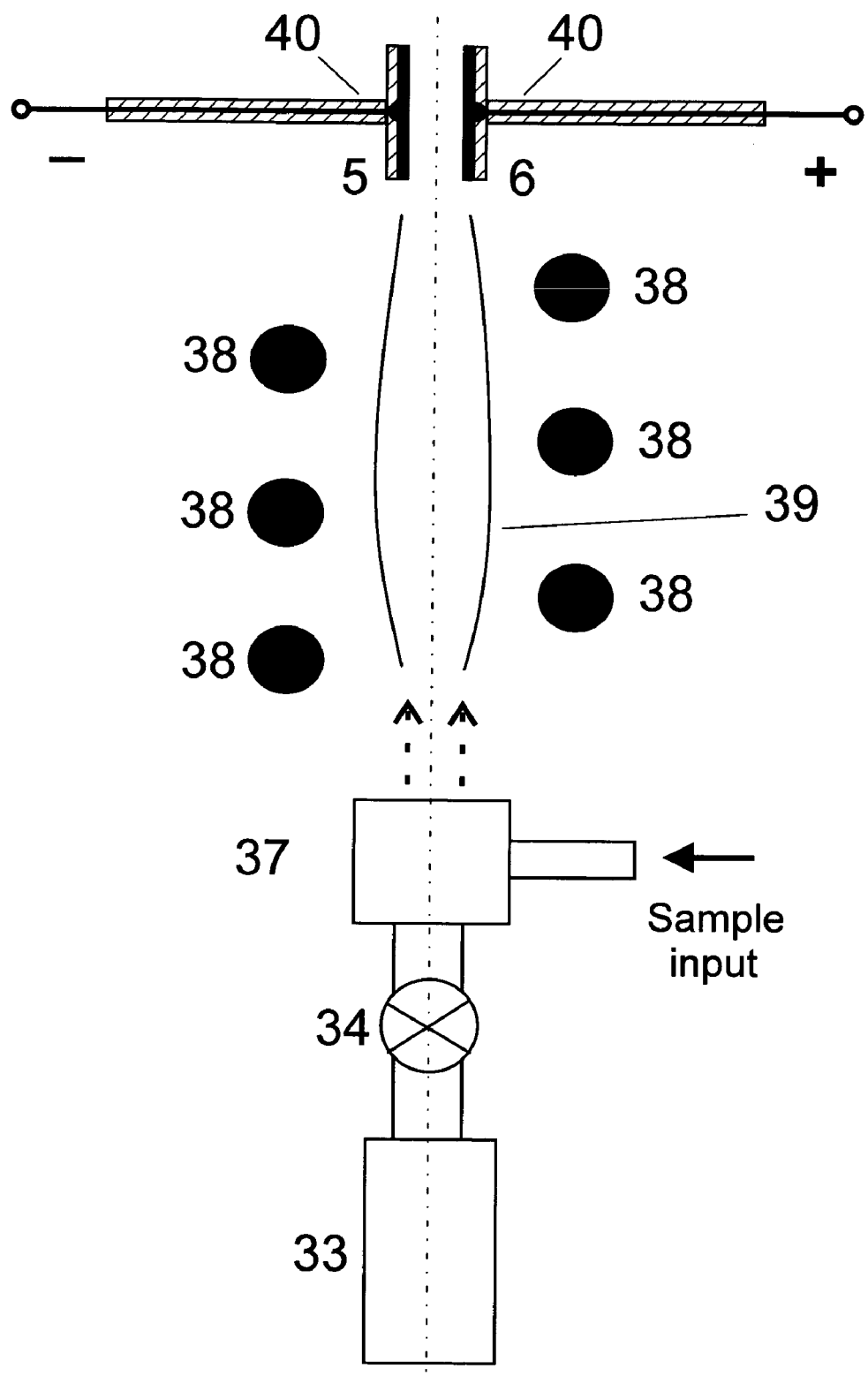
FIG. 8 is a cross section of the ionization detector and a block diagram of the setup for identification of elemental composition of impurities, pre-atomized in an additional gas glow discharge.

FIG. 8 shows a scheme for an elemental composition analysis of a liquid or gaseous sample. A flow of buffer gas, usually a noble gas, from gas container 33 is supplied through the pressure regulator with a valve 34 into a mixing unit 37, where it is blended with the sample flow to be analyzed (the inlet is indicated with an arrow). Further, the mixture is delivered along the inductor coil axis of inductively-coupled plasma (ICP) generator of conventional design (shown with dashed arrows); there are shown cross sections of the coil turns 38. The buffer gas flow from the mixing unit 37 must have a sufficiently high velocity to prevent the atmospheric gas from getting close to the near-axial region of the coil. The ICP generator creates, inside of the coil turns 38, a microwave discharge of such a power that the buffer gas in the near-axial region acquires a temperature of several thousands degrees, providing a thermal decomposition of the sample molecules into atoms. The high temperature region is indicated with contour 39 in FIG. 8. Then, at least one cathode 5-anode 6 pair is positioned below in the flow and is connected to a measuring circuit similar to those in FIGS. 1, 3 and 4 (not shown in FIG. 8). Instead of this, one can also position a pair of electrodes 5 and 6 with a grid between them, as illustrated in FIGS. 2, 5 and 6. The distance between region 39 and electrodes 5 and 6 is chosen such that the flow temperature in the electrodes vicinity has become low enough to avoid their damage but the sample atoms have not had enough time to recombine into molecules. The electrodes are made from chemically inactive metal capable to resist a high temperature. The outer electrodes surfaces and the connecting leads are protected with ceramic insulators 40. The measurement of the current-voltage characteristic and the identification of the sample atoms are performed following one of the variants described above with explanations to FIGS. 1-6. In addition, a microwave discharge may induce electromagnetic noise in the circuits for measuring the current-voltage characteristic; to avoid the noise, one can use a periodic pulse regime of the ICP generator operation and measure the current across electrodes 5 and 6 in the time intervals between the pulses.

Figure 9:
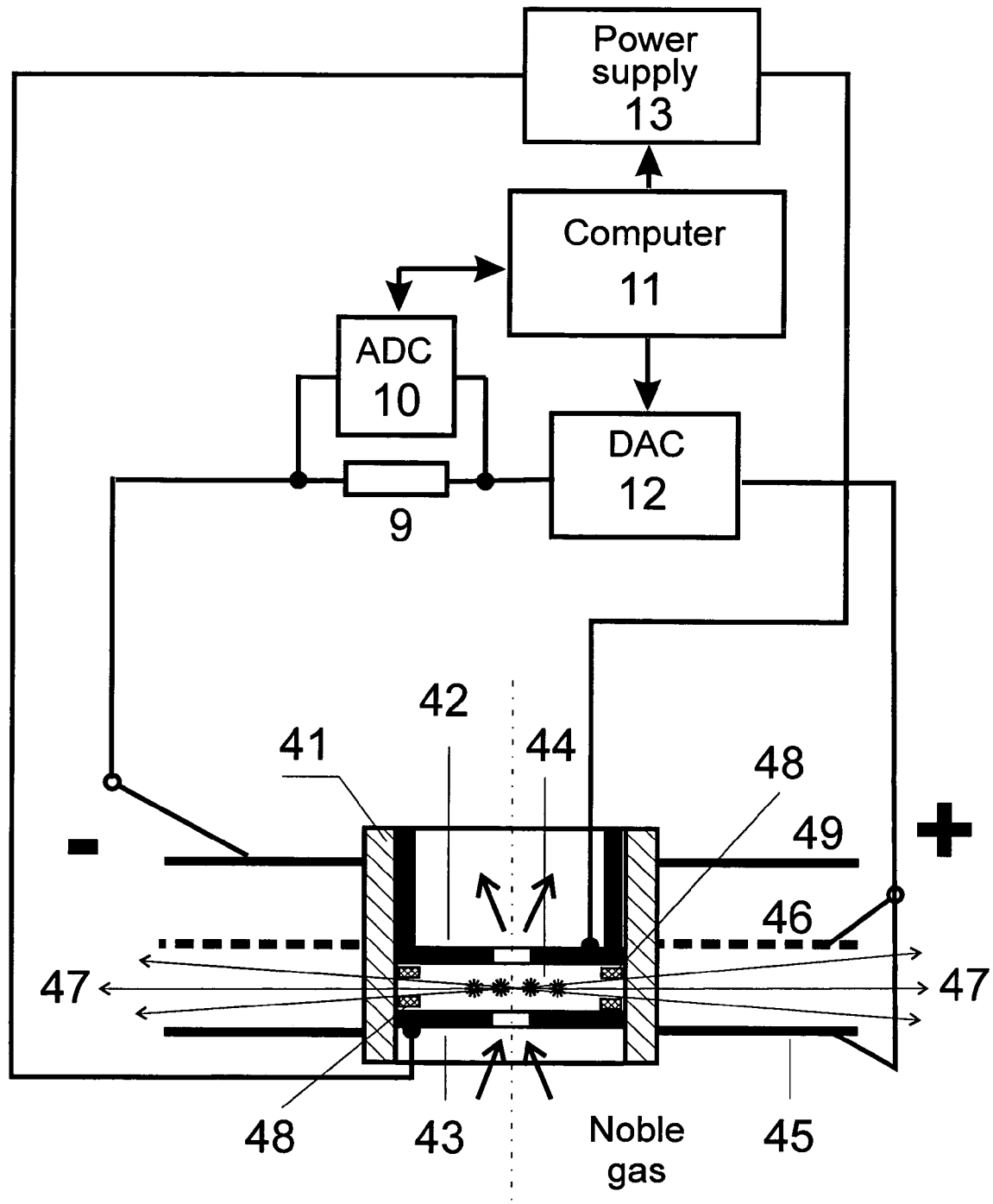
FIG. 9 is a cross section of the ionization detector and a block diagram of the setup for photo-ionization identification of impurities in atmospheric air.

FIG. 9 gives a schematic diagram of the photo-ionization analysis of gas impurities in atmospheric air, using a gas glow discharge source of ultraviolet radiation. The gas discharge chamber comprises a cylindrical window 41 transparent to vacuum ultraviolet radiation (VUV), e.g., up to photons energy of 11.6 eV. The material of the window may be, e.g. LiF. A pulsed or continuous glow discharge is ignited between plane-parallel cylindrical electrodes 42 and 43. A noble gas, for example, Ar or its mixture with He, occupies the discharge chamber or is flowed into it, as shown with arrows. Flow pumping can be used to stabilize the working mixture composition and to remove excess heat. The glow discharge parameters are chosen in such a way that the noble gas atoms radiate predominantly resonant photons of about 11.6 eV having enough narrow line width. The pressure in the discharge chamber may be in the range from $10^2$ Pa up to the atmospheric pressure. At high pressure, an addition of He as a buffer gas can reduce the production rate of Ar eximer molecules which radiate in a rather wide VUV band, lowering the monochromaticity of the photo-ionizing radiation. The glow discharge operating voltage may be 300-500 V and the current about 100 mA. The interelectrode gap can be chosen from the condition of Eq. (4) to provide the discharge stability at the pressures up to the atmospheric one. The power unit 13 of the glow discharge source may operate in a continuous or in a pulsed mode to provide heat removal and to decrease the amount of excited Ar atoms recombining into excimer molecules. All of this is controlled by computer 11. The energy of resonant Ar photons is sufficient for the ionization of many molecules to be detected as impurities in the atmospheric air, but it is too low to ionize the major components of air—oxygen and nitrogen molecules. For this reason, the photoelectron current is largely determined by the impurities ionization, that is increasing the detector sensitivity. In the device suggested, the Ar emission lines of the energy above 11.6 eV are absorbed by the window, and there are no Ar spectral lines with energies less than 11.6 eV but sufficient for molecules photo-ionization, so this photo-ionizing radiation possesses the necessary monochromaticity. It is also possible to use glow discharges in other noble gases and their mixtures to generate predominantly resonant photons of other energies in the VUV region, say, pure neon (using a window transparent to Ne resonant radiation) or krypton, or both gases mixed with He. The resonant photon flux goes from region 44, where the glow discharge is burning, through the window 41 to get into the region between anode 45 and grid 46, which are ring-shaped and are arranged co-axially with the glow discharge chamber. Anode 45 and grid 46 are parallel to each other and are connected electrically to create an equipotential space. Photons trajectories 47 (indicated with arrows) in the region between anode 45 and grid 46 are limited by circular dielectric diaphragms 48, so the photons cannot reach the surface of electrodes 45 and 46 and can not produce an undesirable photo-electron current from their surfaces. The impurity molecules are photo-ionized in the air between electrodes 45 and 46, and the photoelectrons diffuse in the space between anode 45 and grid 46; some of them find their way into the region between the grid 46 and the cathode 49, where they are analyzed with their energy in the electric field, as described above in relation to FIG. 2. The photo-electron current across cathode 49 is measured using resistor 9 and ADC 10 controlled by computer 11. A scanning of the voltage between the cathode 49 and the grid 46 is accomplished by the DAC 12. The gaps between electrodes 45, 46 and 49 are chosen so that the energy loss by electrons in collisions with air molecules prior to electrons recombination on said electrodes would not exceed a level prescribed, say, by Eq. (4). For atmospheric pressure air, the gap between these electrodes may be about 0.1 mm.

INDUSTRIAL APPLICABILITY

The present invention can be used for the analysis of rather arbitrary gas mixtures by adding an appropriate pure buffer gas, until the initial mixture can be considered as an impurity in the buffer gas added, and also for the analysis of gas mixtures produced in the composition identification processes for the of solids and liquids. This invention can be implemented using available (and described in a literature) electronic components

REFERENCES CITED

1. "High Resolution Gas Chromatography", edited by K. J. Hyver, published by Hewlett-Packard Co., 1989.
2. T. A. Carlson. "Photoelectron and Auger Spectroscopy", published by Plenum Press, 1975.
3. Wentworth et al. U.S. Pat. No. 5,317,271.
4. Zhu et al. U.S. Pat. No. 5,192,865.
5. Wentworth et al. U.S. Pat. No. 5,153,519
6. Simon et al. U.S. Pat. No. 5,578,271
7. Stearn et al. U.S. Pat. No. 5,532,599.
8. V. L. Granovsky, "Electric Current in a Gas", Volume 1, published by "Gosudarstvennoe Izdatelstvo Techniko-Teoreticheskoy Literatury", Moscow, 1952, 432 p.

What is claimed is:

1. A method for the analysis of impurities in a main gas comprising:
   (a) an ionization of impurity atoms and molecules in their collisions with particles of definite energy in an ionization chamber;
   (b) measurement of an electric current between at least two electrodes at least one of which is an anode and one of which is a cathode positioned in said chamber, as a function of the voltage applied between said two electrodes;
   (c) selection of a main gas pressure and of said ionization chamber geometry in such that a distance between any point in said chamber and the nearest chamber wall or one of said electrodes is of the order or less than a mean displacement of an electron before it loses a given portion of its kinetic energy;
   (d) providing equipotential space at the region of said ionization chamber, where said ionizing collisions occur;
   (e) determination of amount of electrons with characteristic energies, which are generated in the ionization of said atoms or molecules, from electric current dependence on the voltage applied between said electrodes; and
   (f) identification of said impurities in said main gas from parameters of said electrons.

2. The method of claim 1 wherein said main gas is a noble gas.
3. The method of claim 2 wherein said main gas is helium.
4. The method of claim 1 wherein said main gas pressure may vary from 10 to $10^5$ Pa and above with appropriate change in said ionization chamber geometry.
5. The method of claim 1 wherein a voltage applied between two said electrodes is varied from 0 to the ionization threshold of said main gas, and the amount of said electrons with the characteristic energies is determined from the second derivative of the electric current dependence on the voltage applied.
6. The method of claim 1 wherein said equipotential space is created in said ionization chamber region by using a pulsed power source to produce an afterglow plasma in the ionization chamber; said impurity atoms or molecules are ionized in collisions with metastable atoms or molecules of said main gas, generated under the effect of said pulsed power source; said current is measured with a time delay following the power source effect; and the concentration and temperature of the charged particles in the afterglow plasma at the moment of measurement are provided so that the Debye length is less than the dimensions of said ionization chamber.
7. The method of claim 6 wherein a pulsed glow discharge ignited between said electrodes is used as a said pulsed power source.
8. The method of claim 6 wherein pulsed laser radiation as a said pulsed power source is used to create plasma in the gap between said electrodes.
9. The method of claim 6 wherein said impurity atoms or molecules are ionized when said afterglow plasma is irradiated by photons of a given energy from an external source.
10. The method of claim 9 wherein said impurity atoms or molecules are ionized by irradiation by photons resonant to the atoms or molecules of said main gas.
11. The method of claim 1 wherein said electrodes have a planar shape and are parallel each other.
12. The method of claim 6 wherein said ionization chamber is used with N insulated cathodes positioned inside; an individual voltage with respect to one or several anodes is applied to each cathode; the current across each of the N cathodes is measured; the amount of electrons with the characteristic energy values, which are generated in the ionization of the impurity atoms or molecules, is found from combined data on the currents measured.
13. The method of claim 1 wherein a conducting grid is placed between said electrodes, which is electrically connected to an anode to create an equipotential space between them; the impurity atoms or molecules are ionized by irradiating the space between said grid and said anode by neutral particles of definite energy from an external source.
14. The method of claim 13 wherein said electrodes and said grid have planar shapes and are arranged in parallel.
15. The method of claim 13 wherein the impurity atoms or molecules are ionized by photons resonant to the atoms of said main gas.
16. The method of claim 13 wherein an electric charge passed across a cathode is controlled; when said charge exceeds the prescribed value, said external source is turned off and an electric field is applied until charged particles are removed from said inter-electrode gap; then said external source is turned on and the current is measured again.
17. The method of claim 13 wherein N insulated cathodes are positioned in said ionization chamber; an individual voltage relative to corresponding grids and one or several anodes is applied to each cathode; the individual current across each of the N cathodes is measured; combined measured current values are used to find the amount of electrons with the characteristic energies, produced in the ionization of said impurity atoms or molecules.

18. The method of claim 1 further comprising a process wherein the impurities to be analyzed are provided by a target sample material atomization using with an additional power source; the impurities formed are mixed with said main gas and are delivered into said ionization chamber.

19. The method of claim 18 wherein said target sample is used as a cathode atomized by a preliminary plasma discharge ignited by said additional power source.

20. The method of claim 18 wherein the impurity molecules are pre-dissociated into atoms in an additional plasma discharge and the atomic composition of said impurities is analyzed.

21. An ionization detector for the analysis of the impurities composition in a main gas, comprising:
   (a) an ionization chamber filled with said main gas and impurities mixture and, at least, two electrodes at least one being an anode and one being a cathode inside of said chamber, wherein said main gas pressure and the ionization chamber geometry being chosen in such that a distance from any point inside of said ionization chamber to nearest chamber wall or one of said electrodes is less than a mean displacement of electrons before they lose the chosen portion of their kinetic energy;
   (b) an equipotential space provided at the region of said ionization chamber where said impurities ionization occurs;
   (c) a power source generating particles with definite energy to ionize said impurity atoms or molecules;
   (d) a measuring circuit to detect electric current as a function of the voltage applied to said electrodes wherein said measuring system is capable of determining the amount of electrons with characteristic energies produced during the ionization of said impurities.

22. The ionization detector of claim 21 wherein a noble gas is used as said main gas.

23. The ionization detector of claim 22 wherein helium is used as said main gas.

24. The ionization detector of claim 21, wherein said main gas pressure varies from 10 to $10^5$ Pa and more.

25. The ionization detector of claim 21 wherein the voltage applied between two said electrodes is varied in the range from 0 to the ionization threshold of said main gas, and said measuring system is designed to find second derivative of the current dependence on the voltage applied to determine the amount of electrons with the characteristic energy values.

26. The ionization detector of claim 21 wherein said power source is a pulsed generator to create an afterglow plasma in said ionization chamber; the measuring system is designed to register the electric current with a time delay after the plasma generator pulse; said generator is capable of producing sufficient concentration of metastable atoms of the main gas to register the electrons with the characteristic energies, formed in the impurities ionization by said metastable atoms, said generator is also capable of producing such concentration and temperature of charged particles in the afterglow plasma that the Debye length is less than the dimensions of the ionization chamber at the moment of the current measurement.

27. The ionization detector of claim 26 wherein said power source ignites a pulsed glow discharge between two said electrodes.

28. The ionization detector of claim 26 wherein said power source is a pulsed laser creating plasma between two said electrodes.

29. The ionization detector of claim 26 wherein an additional external source of photons of definite energy is installed to ionize the impurity atoms or molecules in the afterglow plasma.

30. The ionization detector of claim 29 wherein said additional external source generates photons resonant with the atoms or molecules of said main gas.

31. The ionization detector of claim 21 wherein said electrodes are of plane-parallel shape.

32. The ionization detector of claim 21 wherein said ionization chamber comprises N insulated electrodes; an individual voltage is applied to each of said electrodes relative to one or several connected anodes; said measuring system is capable of measuring the individual electric current across each of N said cathodes as a function of the applied voltage.

33. The ionization chamber of claim 21 wherein a conducting grid is positioned between two said electrodes and is electrically connected with said anode to create an equipotential space between them; an external source of neutral particles of a definite energy is installed in such a way that the impurity atoms or molecules are ionized due to the irradiation of the space between said grid and said anode.

34. The ionization detector of claim 33 wherein said electrodes and said grid are plane-parallel to each other.

35. The ionization detector of claim 33 wherein said external source generates photons resonant with the atoms or molecules of said main gas.

36. The ionization detector of claims 33 wherein said measuring system is designed capable of controlling the current across said cathode; when this current exceeds a prescribed value, said measuring system turns off said external source, applies an electric field until the charged particles are removed from said inter-electrode gap, then turns on said external source again and continues to measure the current.

37. The ionization detector of claim 33 wherein said ionization chamber contains N insulated cathodes; individual voltage is applied to each of said cathode relative to corresponding grid and one or several anodes; said measuring system is capable to measure the current across each of said N cathodes individually.

38. The ionization detector of claim 33 wherein said external radiation source further comprises:
   (a) a cylindrical window transparent to this radiation;
   (b) two electrodes covering the butt sides of said window;
   (c) a power source to ignite a glow discharge inside of said cylindrical window between said two electrodes;
   said external radiation source contains argon and is mounted inside of said ionization chamber; said anode, cathode and grid for photoelectrons detection are formed as plane-parallel rings external to said cylindrical window and arranged coaxially with said cylindrical window in such a way that the radiation penetrates only the space between said anode and said grid.

39. The ionization detector of claim 21 wherein an additional power source is used to atomize a sample target material as an impurity into said main gas and there are means for supplying said mixture to said ionization chamber for the composition analysis.

40. The ionization detector of claim 39 wherein said sample target is installed as a cathode for atomization by a preliminary plasma glow discharge ignited by said additional power source.

41. The ionization detector of claim 21 wherein an additional plasma discharge source is used to produce pre-dissociation of sample molecules into atoms for the analysis of the elemental composition of the sample in said ionization chamber.

* * * * *